(12) United States Patent  (10) Patent No.: US 7,314,238 B2
Robert  (45) Date of Patent: Jan. 1, 2008

(54) FLUID CONNECTION

(75) Inventor: Maxime Robert, Quebec (CA)

(73) Assignee: American Sterilizer Company, Mentor, OH (US)

( * ) Notice: Subject to any disclaimer, the term of this patent is extended or adjusted under 35 U.S.C. 154(b) by 643 days.

(21) Appl. No.: 10/857,338

(22) Filed: May 28, 2004

(65) Prior Publication Data

US 2005/0265877 A1    Dec. 1, 2005

(51) Int. Cl.
  *F16L 17/00* (2006.01)
  *F16L 17/06* (2006.01)
  *F16L 37/26* (2006.01)
(52) U.S. Cl. .................. 285/103; 285/101; 285/325
(58) Field of Classification Search ................ 285/95, 285/96, 98, 100, 101, 102, 103, 325, 326, 285/327, 67; 251/157, 172, 186; 277/626
  See application file for complete search history.

(56) References Cited

U.S. PATENT DOCUMENTS

| | | | | |
|---|---|---|---|---|
| 160,700 A | * | 3/1875 | Painter | 285/325 |
| 295,151 A | * | 3/1884 | Cummins | 285/325 |
| 686,571 A | * | 11/1901 | Wilson | 285/67 |
| 823,346 A | * | 6/1906 | Maxwell | 285/325 |
| 2,293,012 A | * | 8/1942 | Barker | 285/96 |
| 2,536,292 A | * | 1/1951 | Kollsman | 277/399 |
| 2,568,092 A | * | 9/1951 | Sloan et al. | 285/101 |
| 3,377,028 A | * | 4/1968 | Bruggeman | 239/394 |
| 3,442,288 A | * | 5/1969 | Scaramucci | 137/515 |
| 4,634,202 A | * | 1/1987 | Taylor | 439/294 |
| 4,941,768 A | * | 7/1990 | Arendt | 403/331 |
| 5,383,689 A | * | 1/1995 | Wolfe, Sr. | 285/124.3 |

FOREIGN PATENT DOCUMENTS

GB    2218350 A  *  11/1989

* cited by examiner

*Primary Examiner*—James M. Hewitt
(74) *Attorney, Agent, or Firm*—Kusner & Jaffe; Michael A. Centanni

(57) ABSTRACT

A fluid connection comprised of a first fitting having a body with a first end and a second end. A passage extends through the body from the first end to the second end. A bracket is mounted to the second end of the body. The bracket defines a space adjacent the second end. A mounting element is provided for mounting the first end of the body to a fluid inlet line. A piston is movable within the passage. The piston has an inlet side facing the first end of the body and an outlet side facing the second end of the body. Apertures through the piston fluidly connect the inlet side of the piston to the outlet side of the piston. A second fitting, having a fluid opening therethrough, is dimensioned to be slidably received within the space adjacent the second end of the fitting. The piston is movable into engagement with the second fitting with the apertures in the piston communicating with the fluid opening in the second fitting.

19 Claims, 3 Drawing Sheets

FLUID CONNECTION

FIELD OF THE INVENTION

The present invention relates to connection fittings for fluid conduits, and more particularly to a quick connect/disconnect connection for use in a washer for microbially decontaminating items.

BACKGROUND OF THE INVENTION

Medical instruments and equipment that are exposed to biological contaminants require microbial decontamination between uses. It is know to microbially decontaminate medical instruments and equipment in washers by exposing the medical instruments or equipment to a liquid microbial decontaminating solution. Known washing systems for microbial decontamination of medical instruments and equipment typically include baskets or racks that retain the various equipment or instruments to be cleaned. The baskets or racks are usually movable within the washer to facilitate loading and unloading of the washer. It is also known to have spray heads mounted to the movable racks or baskets to direct the microbial decontaminating solution over the instruments therein. Some type of fluid connection is therefore required between a stationary fluid inlet line on the washer and a movable fluid line on the rack or basket, or between the stationary fluid inlet line on the washer and some accessory used within the washer.

The present invention provides a fluid connection that is quick and easy to connect and disconnect in a washer for microbially decontaminating medical, surgical or veterinary instruments or equipment.

SUMMARY OF THE INVENTION

In accordance with a preferred embodiment of the present invention, there is provided a quick connect/disconnect connection for a fluid line comprised of a body having a first end and a second end. The first end of the body is connectable to a stationary fluid inlet line. A passage extends through the body, and a piston is movable within the passage. The piston has an inlet side and an outlet side. The inlet side has a surface oriented toward the fluid inlet to be exposed to pressurized fluid from the fluid inlet. Apertures through the piston fluidly connect the inlet side of the piston to the outlet side of the piston. A bracket element is mounted to the second end of the body and defines a space adjacent the second end. A movable fitting, having a fluid opening connectable to a fluid supply line, is dimensioned to be received within the space adjacent the body. The piston is movable into engagement with the fitting with the apertures in the piston communicating with the fluid opening in the fitting when the inlet side of the piston is exposed to fluid pressure in the inlet line.

In accordance with the present invention, there is provided a fluid connection comprised of a first fitting having a body with a first end and a second end. A passage extends through the body from the first end to the second end. A bracket is mounted to the second end of the body. The bracket defines a space adjacent the second end. A mounting element is provided for mounting the first end of the body to a fluid inlet line. A piston is movable within the passage. The piston has an inlet side facing the first end of the body and an outlet side facing the second end of the body. Apertures through the piston fluidly connect the inlet side of the piston to the outlet side of the piston. A second fitting, having a fluid opening therethrough, is dimensioned to be slidably received within the space adjacent the second end of the fitting. The piston is movable into engagement with the second fitting with the apertures in the piston communicating with the fluid opening in the second fitting.

One advantage of the present invention is a fluid connection that is quickly and easily connected and disconnected.

Another advantage of the present invention is a fluid connection as described above for use in a washer for microbially cleaning and decontaminating items.

These and other objects will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
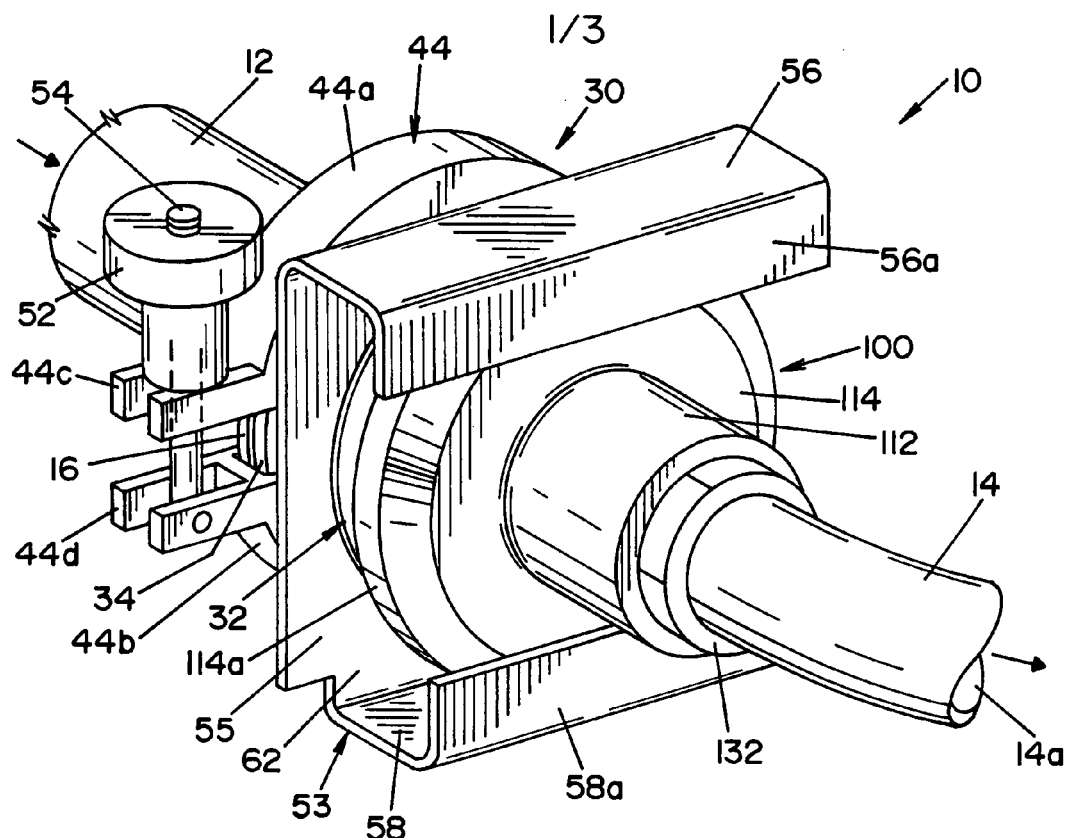
FIG. 1 is a perspective view of the fluid connection for connecting fluid conduit in a washer for microbially decontaminating items, illustrating a preferred embodiment of the present invention.
Figure 2:
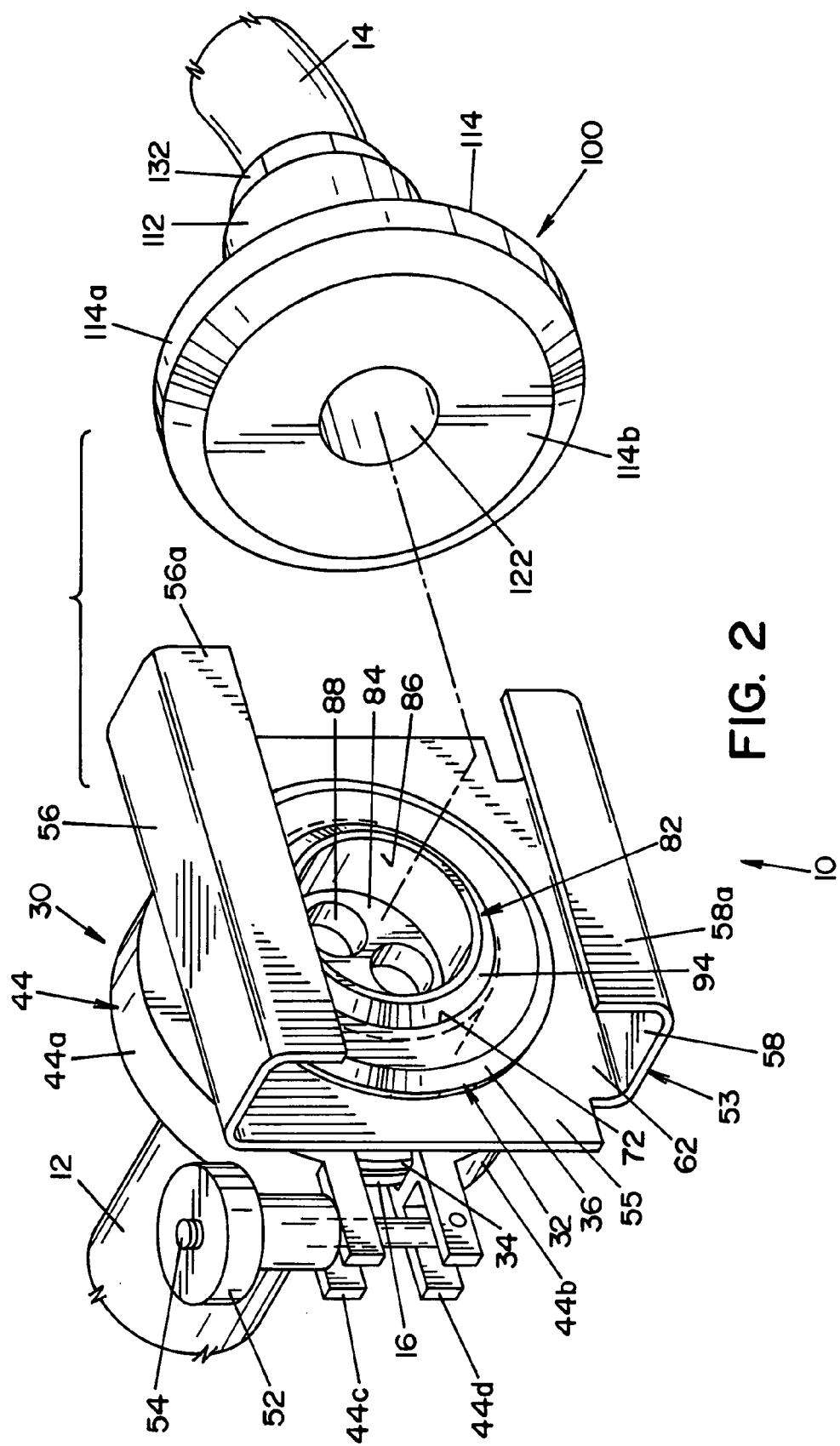
FIG. 2 is a perspective view showing first fitting attached to a stationary fluid inlet and second fitting attached to a removable accessory.

Referring now to the drawings wherein the showings are for the purpose of illustrating a preferred embodiment of the invention only, and not for the purpose of limiting same, FIG. 1 shows a fluid connection 10, illustrating a preferred embodiment of the present invention. Fluid connection 10 is basically comprised of a first, stationary fitting 30 for attachment to a stationary fluid inlet line or conduit 12 and a second, accessory fitting 100 for attachment to a fluid supply line or conduit 14, as best seen in FIG. 2, wherein fittings 30, 100 are shown spaced-apart from each other. Stationary fluid inlet line 12 has a fluid opening 12a extending therethrough. Fluid supply line 14 has a fluid opening 14a extending therethrough. As used herein, the term "stationary fitting" refers to a fitting that is adapted to be connected to a stationary fluid inlet line, such as, by way of example and not limitation, a stationary water inlet pipe on a microbial deactivation washer (not shown). Such inlet line typically extends into the interior cavity of a washer for connection to an accessory, such as spray heads on a rack or basket (not shown), used in the washer. As used herein, the term "movable fitting" refers to a fitting adapted to be attached to a fluid supply conduit that is movable relative to a stationary fluid inlet line, such as, by way of example and not limitation, a fluid supply line to a spray on a movable basket used in the washer, or to an instrument or piece of equipment to be washed in a movable basket within the washer. In this respect, the accessory above may be a spray head or an instrument on a rack or basket that is movable within the washer.

Figure 3:
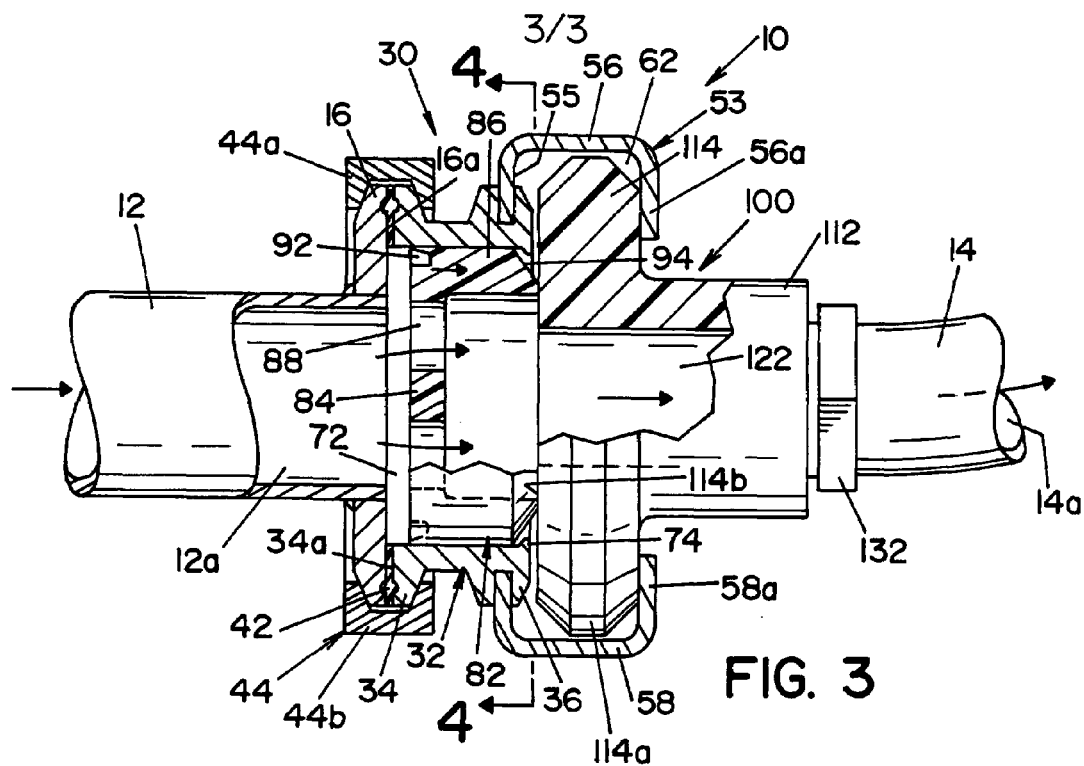
FIG. 3 is a partially sectioned, elevational view of the fluid connection shown in FIG. 1.
Figure 4:
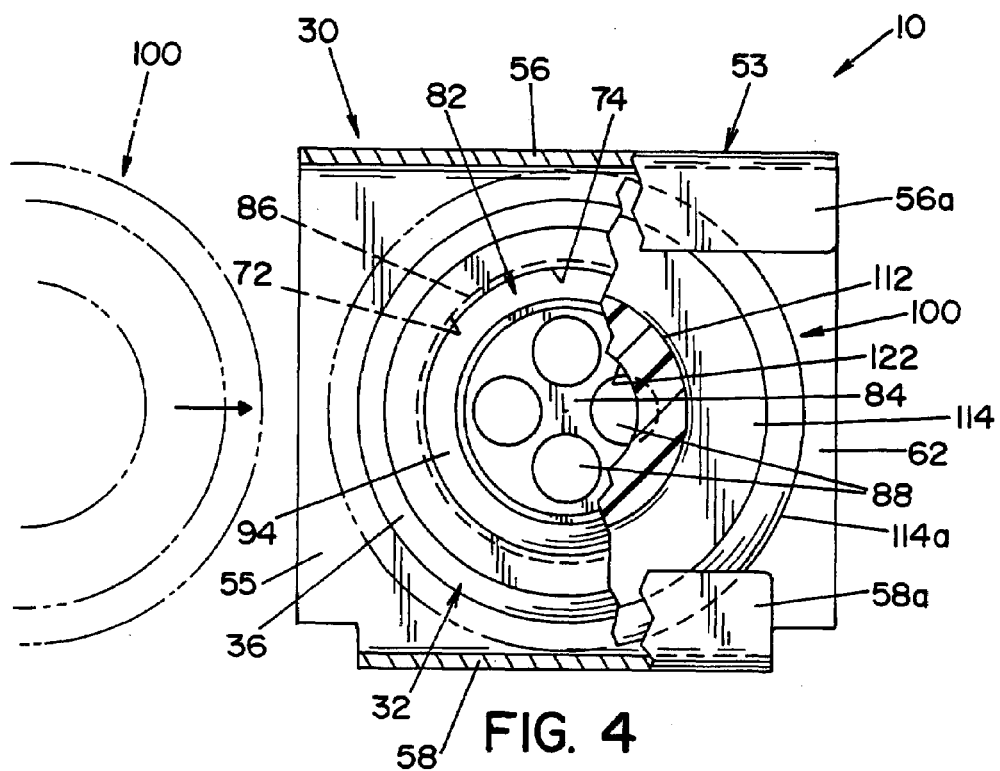
FIG. 4 is a section view taken along lines 4-4 of FIG. 3.

In the embodiment shown, first, stationary fitting 30 includes a piston body 32, best seen in FIG. 3. Piston body 32 is cylindrical in shape and includes an outwardly extending annular flange 34 at one end and an outwardly extending boss or mount 36 at the other end.

Flange 34 has a planar surface 34a dimensioned to mate with a planar surface 16a on a flange element 16 of stationary fluid inlet line 12. An annular seal 42 is disposed between flange 34 on piston body 32 and flange 16 on stationary fluid inlet line 12 to form a fluid seal therebetween. Flanges 34 and flange element 16 are held together by a conventional collar clamp 44 comprised of clamp sections 44a, 44b, that are hinged together at one end (not shown) and have slotted tabs 44c, 44d at the other end. A thumbnut 52 and a thread rod 54 attached to slotted tab 44d are used to secure collar section 44a, 44b onto flanges 34 on piston body 32 and flange element 16 on stationary fluid inlet line 12. As best seen in FIG. 3, flange 34 and flange element 16 have beveled edges to matingly engage tapered inner surfaces along the inner edge of collar clamp sections 44a, 44b. In this respect, tightening collar clamp 44 forces flange 34 and flange element 16 towards each other thereby forming a fluid-tight seal between stationary fluid inlet line 16 and piston body 32, in a manner conventionally known.

Annular mount 36 on piston body 32 has a generally C-shaped bracket 53 secured thereto. Bracket 53 is preferably formed from a metallic sheet material that is bent into a generally C-shaped configuration. Bracket 53 has a planar base 55 and sides 56, 58 that are generally L-shaped. Sides 56, 58 have inwardly turned ends 56a, 58a. A generally rectangular slot or space 62 is formed between planar base 55 and ends 56a, 58a of C-shaped bracket 53 and the inwardly turned ends.

Piston body 32 defines a cylindrical inner cavity 72 that communicates with opening 12a in stationary fluid inlet line 12, and that extends through C-shaped bracket 53 to communicate with slot 62 defined by C-shaped bracket 53. An inwardly extending lip 74 is formed at one end of piston body 32, as best seen in FIG. 3. Lip 74 is formed on the end of piston body 32 where C-shaped bracket 53 is connected to piston body 32.

Figure 5:
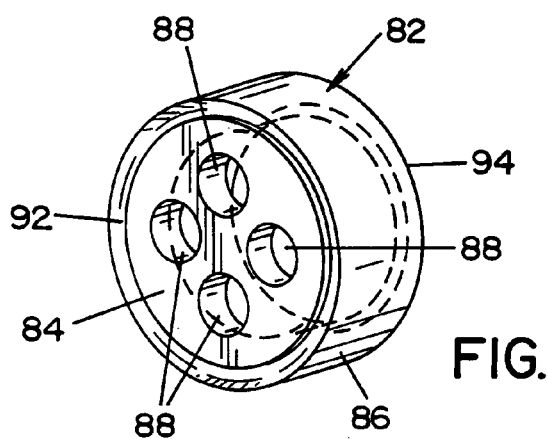
FIG. 5 is a perspective view of a piston used in the fluid connection shown in FIGS. 1-4.

Piston cavity 72 is dimensioned to receive a piston 82, best seen in FIG. 5. Piston 82 is generally cylindrical in shape. Piston 82 may be a solid cylindrical plug, but in the embodiment shown, piston 82 is generally C-shaped. In this respect, piston 82 includes a bottom wall 84 and an annular, cylindrical side wall 86 extending to one side of bottom wall 84. A plurality of spaced-apart apertures 88 are formed in bottom wall 84, as best seen in FIG. 5. Apertures 88 are dimensioned such that the total cross-sectional area of all apertures 88 is less than the cross-sectional area of opening 12a of stationary fluid inlet line 12. In the illustrated embodiment, an annular slot 92 is formed in the end face of bottom wall 84 along the periphery thereof. In an alternative embodiment, annular slot 92 may be omitted. The free end of side wall 86 is tapered to form a conical-shaped end 94, as best seen in FIG. 3. By way of example, and not limitation, piston 82 may be formed of teflon or stainless steel.

Referring now to FIG. 2, accessory fitting 100 is best seen. Accessory fitting 100 is a tubular member comprised of a cylindrical body 112 having an outwardly extending flange 114 at one end thereof. Body 112 has a cylindrical opening 122 extending therethrough. Flange 114 has an outer edge 114a that is tapered, and a planar end surface 114b. Second, accessory fitting 100 is dimensioned to be attached to fluid supply line 14 by a conventional hose or tube fitting 132, as illustrated in the drawings. Accessory fitting 100 is dimensioned to be slidably received within rectangular space 62 defined by C-shaped bracket 53 of first, stationary fitting 30.

Referring now to the operation of fluid connection 10, first, stationary fitting 30 is attached to stationary fluid inlet line 12 by means of collar clamp 44. Second, accessory fitting 100 is positioned adjacent first, stationary fitting 30 by sliding flange 114 on cylindrical body 112 into space or slot 62 defined by C-shaped bracket 53. Second, accessory fitting 100 is positioned such that cylindrical opening 122 is aligned with piston cavity 72 in piston body 32. In this respect, cylindrical opening 122 of second, accessory fitting 100 is basically in axial alignment with the axis of cylindrical piston 82. During the operation of the washer, pressurized fluid flows through stationary fluid inlet line 12 into cavity 72 of piston body 32. Since apertures 88 and piston 82 in total define a smaller, cross-sectional area than the cross-sectional area of opening 12a of stationary fluid inlet line 12, a pressure build up will occur within cavity 72 in piston body 32. The pressure on the face of bottom wall 84 of piston 82 forces piston 82 in a direction towards surface 114b of flange 114. In this respect, conical end 94 of piston 82 is forced against surface 114b of flange 114 forming a fluid connection therewith. Fluid flows through apertures 88 into cylindrical opening 122 of cylindrical body 112 of second, accessory fitting 100. From there, pressurized fluid flows through opening 14a of fluid supply line 14 to an accessory device within the washer. Following completion of a washing cycle, the flow of pressurized fluid through stationary fluid inlet line 12 is discontinued. As a result, pressure no longer exists against bottom wall 84 of piston 82 to force piston 82 against surface 114a on flange 114 of second, accessory fitting 100. As a result, second, accessory fitting 100 may be disconnected from first, stationary fitting 30 by sliding fitting 100 out of slot 62 defined by C-shaped bracket 53. The present invention thus provides a quick connect and quick disconnect fluid connection wherein fluid pressure during operation effectively forms a fluid connection between first, stationary fitting 30 and second, accessory fitting 100 by forcing piston 82 into engagement with surface 114b of second, accessory fitting 100.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

The invention claimed is:

1. A quick connect/disconnect connection for a fluid line, comprised of:
   a body having a first end and a second end, said first end being connectable to a stationary fluid inlet line;
   a passage extending through said body;
   a piston movable within said passage, said piston having an inlet side and an outlet side, said inlet side having a surface oriented toward said fluid inlet line to be exposed to pressurized fluid from said fluid inlet line;
   apertures through said piston fluidly connecting said inlet side of said piston to said outlet side of said piston;

bracket means mounted to said second end of said body defining a space adjacent said second end; and a movable fitting having a fluid opening connectable to a fluid supply line, said fitting dimensioned to be received within said space adjacent said body, wherein said piston is movable into engagement with said fitting with said apertures in said piston communicating with said fluid opening in said fitting when said inlet side of said piston is exposed to fluid pressure in said inlet line.

2. A quick connect/disconnect connection as defined in claim 1, wherein said body and said passage therein are cylindrical in shape.

3. A quick connect/disconnect connection as defined in claim 2, wherein said piston is generally cup-shaped and has a bottom wall defining said surface and an annular, cylindrical side wall extending therefrom.

4. A quick connect/disconnect connection as defined in claim 3, wherein said first end of said body includes a flange for mounting said body to said fluid inlet line.

5. A quick connect/disconnect connection as defined in claim 4, wherein said first end of said body is attachable to said fluid inlet line by a collar clamp.

6. A quick connect/disconnect connection as defined in claim 1, wherein said piston forms a seal against a surface on said fitting.

7. A quick connect/disconnect connection as defined in claim 6, wherein said surface on said fitting is a planar surface.

8. A quick connect/disconnect connection as defined in claim 1, wherein said bracket means is a generally C-shaped plate defining a generally rectangular space, and said fitting is a flanged component dimensioned to be slidably received in said rectangular space.

9. A quick connect/disconnect connection as defined in claim 8, wherein said fitting includes a cylindrical body having an annular outwardly extending flange at one end of said cylindrical body, said flange having a planar end surface.

10. A quick connect/disconnect connection as defined in claim 1, wherein the apertures in said piston are dimensioned such that the total cross-sectional area of the apertures is less than the cross-sectional area of said stationary fluid inlet line.

11. A fluid connection comprised of:
a first fitting having a body with a first end and a second end;
a passage extending through said body from said first end to said second end;
a bracket mounted to said second end of said body, said bracket defining a space adjacent said second end;
mounting means for mounting said first end to a stationary fluid inlet line;
a piston movable within said passage, said piston having an inlet side facing said first end of said body and an outlet side facing said second end of said body;
apertures through said piston fluidly connecting said inlet side of said piston to said outlet side of said piston; and
a second fitting having a fluid opening therethrough, said second fitting being dimensioned to be slidably received within said space adjacent said second end of said fitting, wherein said piston is movable into engagement with said second fitting with the apertures in said piston communicating with the fluid opening in said second fitting.

12. A fluid connection as defined in claim 11, wherein said piston is generally cup-shaped and has a bottom wall defining a surface and an annular, cylindrical side wall extending therefrom.

13. A fluid connection as defined in claim 12, wherein said first end of said body includes a flange for mounting said body to said fluid inlet line.

14. A fluid connection as defined in claim 13, wherein said first end of said body is attached to said fluid inlet line by a collar clamp.

15. A fluid connection as defined in claim 14, wherein said piston forms a seal against a surface on said second fitting.

16. A fluid connection as defined in claim 15, wherein said surface on said second fitting is a planar surface.

17. A fluid connection as defined in claim 11, wherein said bracket is a generally C-shaped plate defining a generally rectangular space, and said second fitting is a flanged component dimensioned to be slidably received in said rectangular space.

18. A fluid connection as defined in claim 17, wherein said second fitting includes a cylindrical body having a an annular outwardly extending flange at one end of said cylindrical body, said flange having a planar end surface.

19. A fluid connection as defined in claim 18, wherein the apertures in said piston are dimensioned such that the total cross-sectional area of the apertures is less than the cross-sectional area of said stationary fluid inlet line.

* * * * *